United States Patent
Miyachi

(10) Patent No.: US 12,369,885 B2
(45) Date of Patent: Jul. 29, 2025

(54) ULTRASOUND DIAGNOSTIC APPARATUS AND OPERATION METHOD THEREOF

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

(21) Appl. No.: 18/188,111

(22) Filed: Mar. 22, 2023

(65) Prior Publication Data
US 2023/0309956 A1 Oct. 5, 2023

(30) Foreign Application Priority Data
Mar. 30, 2022 (JP) ................................. 2022-056452

(51) Int. Cl.
*A61B 8/00* (2006.01)
*G01S 7/52* (2006.01)

(52) U.S. Cl.
CPC .......... *A61B 8/4254* (2013.01); *A61B 8/4488* (2013.01); *A61B 8/463* (2013.01); *A61B 8/54* (2013.01); *G01S 7/52068* (2013.01)

(58) Field of Classification Search
CPC ..... A61B 8/4254; A61B 8/4488; A61B 8/463; A61B 8/54; A61B 8/465; A61B 8/483; A61B 8/4477; A61B 8/00; A61B 8/4444; G01S 7/52068; A61N 7/00
See application file for complete search history.

(56) References Cited

U.S. PATENT DOCUMENTS

| | | | | |
|---|---|---|---|---|
| 2002/0143275 A1* | 10/2002 | Sarvazyan | ............. | A61B 5/036 600/587 |
| 2009/0048520 A1* | 2/2009 | Marteau | ............. | G01S 15/8909 600/459 |
| 2010/0286527 A1* | 11/2010 | Cannon | .................... | A61B 8/42 600/459 |

(Continued)

FOREIGN PATENT DOCUMENTS

| | | |
|---|---|---|
| JP | 2011-500253 A | 1/2011 |
| WO | 2012/063420 A1 | 5/2012 |

OTHER PUBLICATIONS

The extended European search report issued by the European Patent Office on Aug. 24, 2023, which corresponds to European Patent Application No. 23165486.4-1126 and is related to U.S. Appl. No. 18/188,111.

*Primary Examiner* — Pascal M Bui Pho
*Assistant Examiner* — Michael Yiming Fang
(74) *Attorney, Agent, or Firm* — Studebaker Brackett PLLC

(57) ABSTRACT

An ultrasound diagnostic apparatus includes an ultrasound probe including a housing in which a first transducer array is disposed at one end and a second transducer array is disposed at the other end, a sensor that is provided in the housing and outputs information for acquiring motion information of the ultrasound probe or angle information of the ultrasound probe, and a processor that acquires used array information indicating which of the first transducer array and the second transducer array is used. The processor is configured to acquire the motion information or the angle information based on the output of the sensor and determine a motion or a position of the ultrasound probe with respect to a subject based on the acquired motion information or angle information and the used array information.

12 Claims, 9 Drawing Sheets

(56) References Cited

U.S. PATENT DOCUMENTS

| | | | |
|---|---|---|---|
| 2010/0298713 A1 | 11/2010 | Robinson | |
| 2013/0018263 A1 | 1/2013 | Kimoto et al. | |
| 2014/0303501 A1* | 10/2014 | Jin | A61B 8/4427 |
| | | | 600/459 |
| 2016/0155227 A1* | 6/2016 | Chae | A61B 8/5223 |
| | | | 382/131 |
| 2017/0258445 A1* | 9/2017 | Van Alphen | A61B 8/4472 |
| 2019/0239852 A1* | 8/2019 | Forzoni | A61B 8/4455 |
| 2021/0386405 A1* | 12/2021 | Oka | A61B 8/468 |
| 2022/0233167 A1* | 7/2022 | Harker | A61B 8/4444 |
| 2022/0338836 A1* | 10/2022 | Doron | A61B 8/5223 |

* cited by examiner

ULTRASOUND DIAGNOSTIC APPARATUS AND OPERATION METHOD THEREOF

CROSS-REFERENCE TO RELATED APPLICATIONS

This application is based upon and claims the benefit of priority from prior Japanese patent application No. 2022-056452, filed on Mar. 30, 2022, the entire contents of which are incorporated herein by reference.

BACKGROUND OF THE INVENTION

1. Field of the Invention

The present invention relates to an ultrasound diagnostic apparatus and an operation method thereof.

2. Description of the Related Art

JP2011-500253A describes an ultrasound transducer assembly including a housing, a plurality of individual ultrasound image data acquisition transducer arrays disposed to the housing, a transducer controller assembly, which is disposed to the housing, that telecommunications with each of the plurality of ultrasound image data acquisition transducer arrays, a communication assembly, which is disposed to the housing, that telecommunications with the transducer controller assembly, and a selection unit that indicates a selected ultrasound image data acquisition transducer array among the plurality of ultrasound image data acquisition transducer arrays for the transducer controller assembly.

WO2012/063420A describes an ultrasound diagnostic apparatus that obtains and displays an angle of an ultrasound probe in a case where a subject is being diagnosed by using an acceleration sensor provided in the ultrasound probe.

SUMMARY OF THE INVENTION

An object of the present invention is to correctly recognize a use state of an ultrasound probe having a plurality of transducer arrays.

An ultrasound diagnostic apparatus according to an aspect of the present invention comprises an ultrasound probe including a housing in which a first transducer array is disposed at one end and a second transducer array is disposed at the other end, a sensor that is provided in the housing and outputs information for acquiring motion information of the ultrasound probe or angle information of the ultrasound probe, and a processor that acquires used array information indicating which of the first transducer array and the second transducer array is used. The processor is configured to acquire the motion information or the angle information based on the information outputted by the sensor and determine a motion or a position of the ultrasound probe with respect to a subject based on the motion information or the angle information and the used array information.

An operation method of an ultrasound diagnostic apparatus according to an aspect of the present invention comprises, in an ultrasound probe including a housing in which a first transducer array is disposed at one end and a second transducer array is disposed at the other end, acquiring used array information indicating which of the first transducer array and the second transducer array is used, and, based on information outputted by a sensor that is provided in the housing and outputs information for acquiring motion information of the ultrasound probe or angle information of the ultrasound probe, acquiring the motion information or the angle information and determining a motion or a position of the ultrasound probe with respect to a subject based on the motion information or the angle information and the used array information.

According to the present invention, a use state of an ultrasound probe having a plurality of transducer arrays can be correctly recognized.

DESCRIPTION OF THE PREFERRED EMBODIMENTS

In the present specification, each of "identical", "same", and "match" is assumed to include an error range generally allowed in the technical field.

Figure 1:
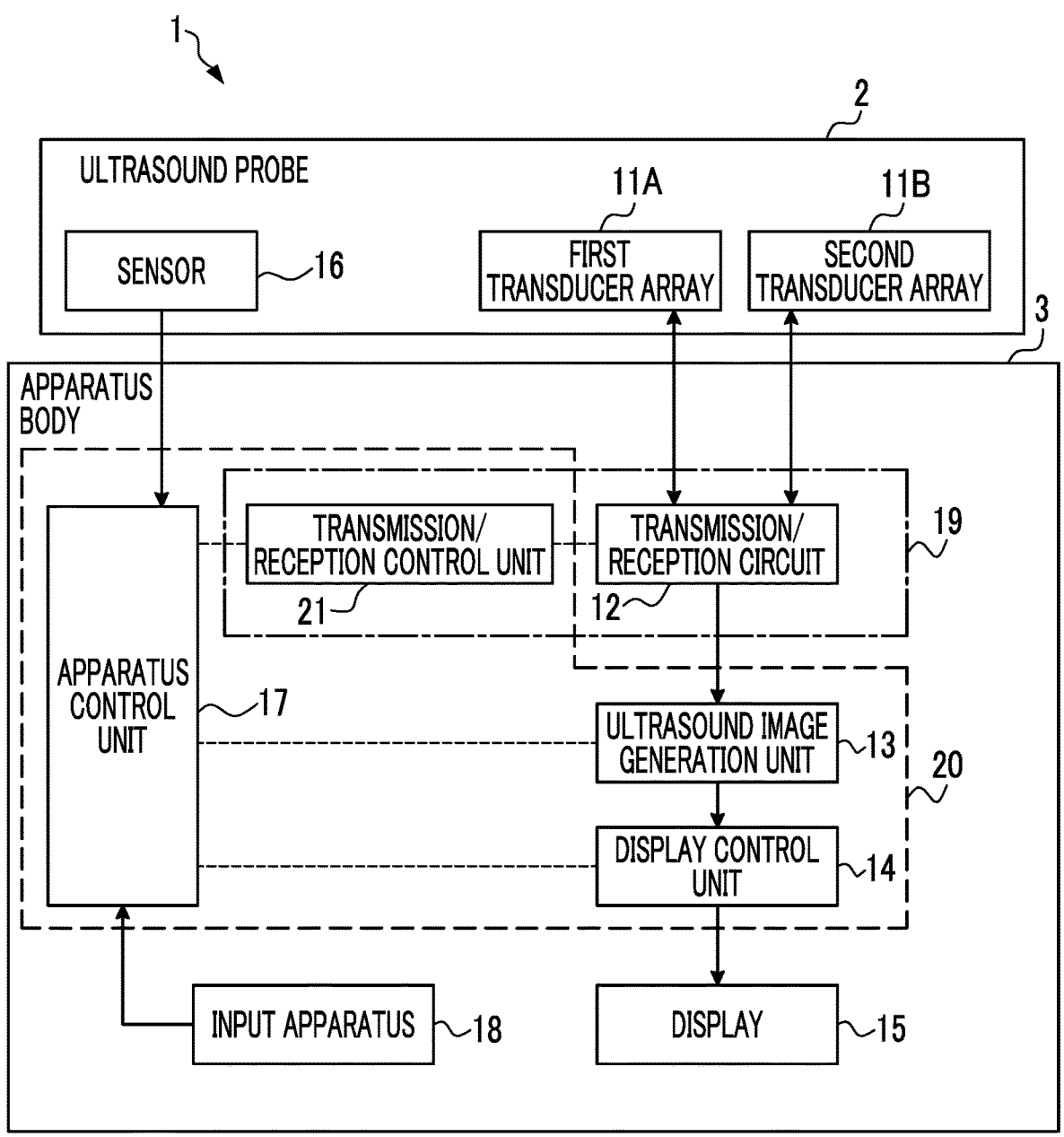
FIG. 1 is a diagram showing a schematic configuration of an ultrasound diagnostic apparatus 1 according to an embodiment of the present invention.
Figure 2:
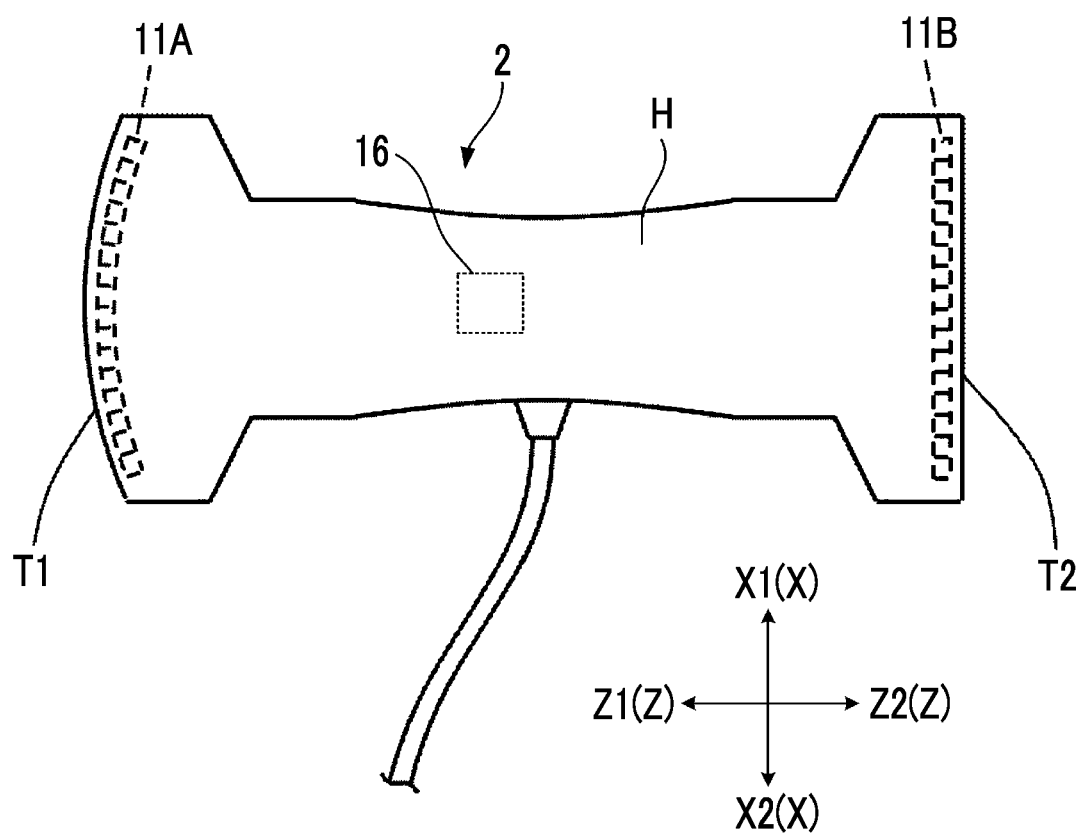
FIG. 2 is a schematic diagram showing a configuration example of an ultrasound probe 2 in the ultrasound diagnostic apparatus 1 shown in FIG. 1.
Figure 3:
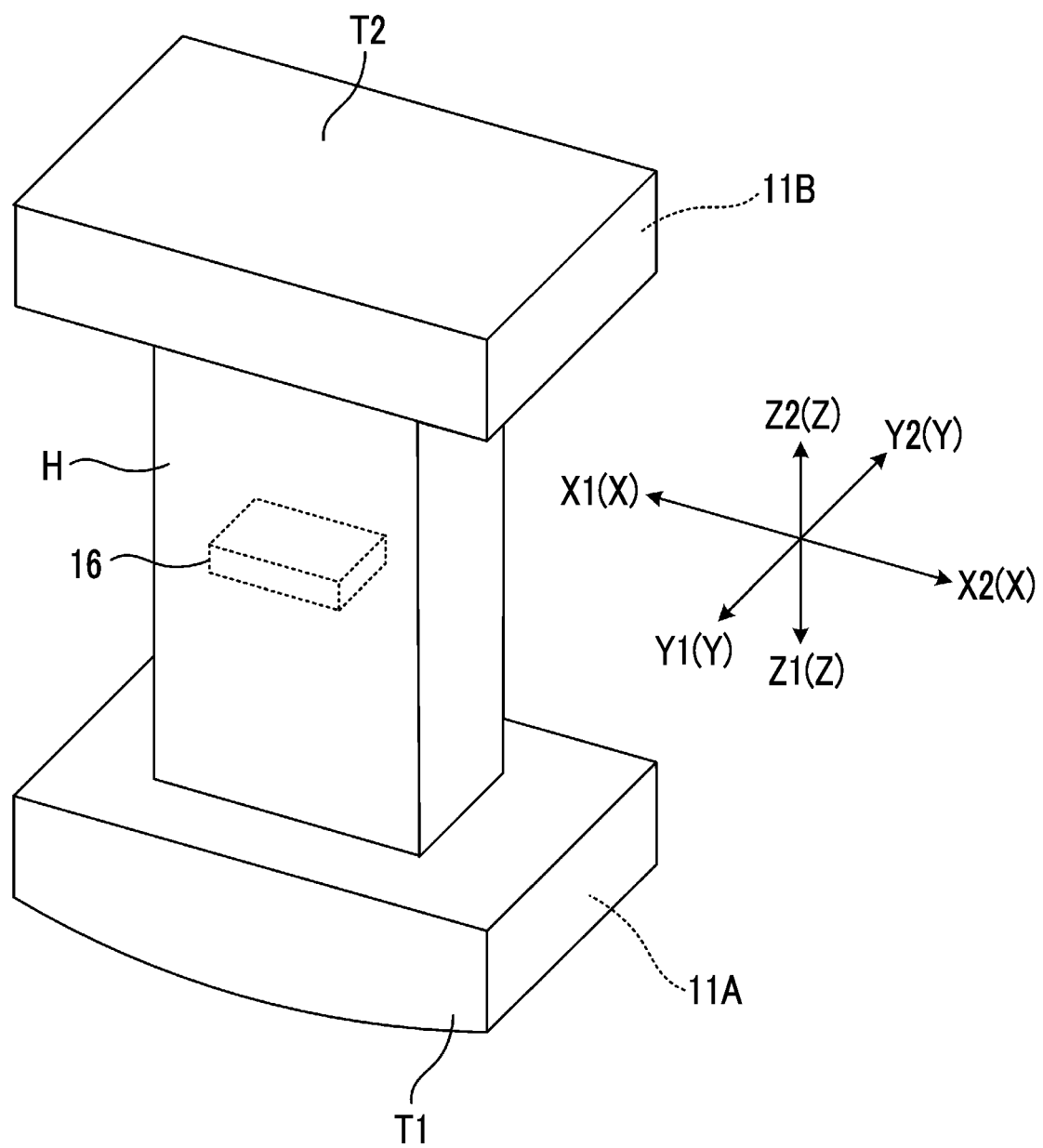
FIG. 3 is a schematic perspective view of the ultrasound probe 2 shown in FIG. 2.

FIG. 1 is a diagram showing a schematic configuration of an ultrasound diagnostic apparatus 1 according to an embodiment of the present invention. FIG. 2 is a schematic diagram showing a configuration example of an ultrasound probe 2 in the ultrasound diagnostic apparatus 1 shown in FIG. 1. FIG. 3 is a schematic perspective view of the ultrasound probe 2 shown in FIG. 2. FIG. 3 shows three directions orthogonal to each other of an X direction, a Y direction, and a Z direction. In FIG. 3, one side of the X direction is described as an X1 direction, the other side thereof is described as an X2 direction, one side of the Y direction is described as a Y1 direction, the other side thereof is described as a Y2 direction, and one side of the Z direction is described as a Z1 direction and the other side thereof is described as a Z2 direction.

As shown in FIG. 1, the ultrasound diagnostic apparatus 1 comprises the ultrasound probe 2 and an apparatus body 3 connected to the ultrasound probe 2. The ultrasound probe 2 comprises a first-type first transducer array 11A connected to the apparatus body 3 and a second-type second transducer array 11B connected to the apparatus body 3. Here, the first transducer array 11A and the second transducer array 11B are each one of types such as a so-called convex transducer array, a linear transducer array, and a sector transducer array, and are types different from each other.

As shown in FIGS. 2 and 3, the ultrasound probe 2 comprises a housing H that supports the first transducer array 11A and the second transducer array 11B. A longitudinal direction of the housing H matches the Z direction. The first transducer array 11A is disposed at one end T1 of the housing H in the Z direction. The second transducer array 11B is disposed at the other end T2 of the housing H in the Z direction. The example of FIG. 2 shows that the first transducer array 11A is the convex transducer array and the second transducer array 11B is the linear transducer array. Each of the first transducer array 11A and the second transducer array 11B includes at least one oscillator column in which a plurality of ultrasound oscillators are arranged along the X direction.

The ultrasound probe 2 comprises a sensor 16 built in the housing H. The sensor 16 outputs information for acquiring motion information or angle information of the ultrasound probe 2 (in other words, housing H). The motion information includes at least a moving direction of the ultrasound probe 2. The angle information refers to information on an angle of the ultrasound probe 2 with respect to a vertical direction. The information for acquiring the motion information or the angle information is, for example, acceleration, angular velocity, or the like. The sensor 16 is configured of, for example, an acceleration sensor, an angular velocity sensor, or a combination of the two sensors. Hereinafter, the sensor 16 will be described as being a 3-axis acceleration sensor.

The sensor 16 detects and outputs the respective accelerations in the X direction, the Y direction, and the Z direction. In the X direction, the sensor 16 can distinguishingly detect the acceleration in the X1 direction and the X2 direction. In the Y direction, the sensor 16 can distinguishingly detect the acceleration in the Y1 direction and the Y2 direction. In the Z direction, the sensor 16 can distinguishingly detect the acceleration in the Z1 direction and the Z2 direction. The acceleration in each direction detected by the sensor 16 is processed to acquire the motion information indicating which direction of the six directions of the X1 direction, the X2 direction, the Y1 direction, the Y2 direction, the Z1 direction, and the Z2 direction the housing H moves. Further, processing of converting the acceleration in each direction detected by the sensor 16 into an angle is performed to acquire the angle information of the housing H. In the conversion of the acceleration information into the angle information, for example, with calculation of an angle in each axial direction with respect to a gravity acceleration direction from acceleration data of each axis with respect to a gravity acceleration of the 3-axis acceleration sensor, angle data of the 3-axis acceleration sensor may be derived and information on a mounting positional relationship between the 3-axis acceleration sensor and the housing H may be added to the angle data to perform the conversion into the angle information of the housing H.

As shown in FIG. 1, the apparatus body 3 comprises a transmission/reception circuit 12 connected to the first transducer array 11A and the second transducer array 11B, a processor 20, a display 15 such as a liquid crystal display (LCD) or an organic electroluminescence (EL) display, and an input apparatus 18 configured by apparatuses for performing an input operation by a user, such as a button, a switch, a touch pad, and a touch panel.

The processor 20 is a central processing unit (CPU) which is a general-purpose processor that executes software (program) to perform various functions, a programmable logic device (PLD) whose circuit configuration is changeable after manufacturing such as a field programmable gate array (FPGA), a dedicated electric circuit which is a processor having a circuit configuration exclusively designed to execute specific processing such as an application specific integrated circuit (ASIC), or the like. The processor 20 may be configured of one processor or a combination of two or more processors having the same type or different types (for example, a plurality of FPGAs, or a combination of CPU and FPGA). In a case where the processor 20 is configured of a plurality of processors, each processor may not be in the same apparatus or may be in another place connected via a network. A hardware structure of the processor 20 is, more specifically, circuitry obtained by combining circuit elements such as a semiconductor element.

The processor 20 executes a program to function as an ultrasound image generation unit 13, a display control unit 14, an apparatus control unit 17, and a transmission/reception control unit 21. The transmission/reception circuit 12 and the transmission/reception control unit 21 constitute an ultrasound image data acquisition unit 19. The information output from the sensor 16 and the information input from the input apparatus 18 are input to the apparatus control unit 17.

The first transducer array 11A and the second transducer array 11B of the ultrasound probe 2 have the plurality of ultrasound oscillators arranged one-dimensionally or two-dimensionally. Each of these ultrasound oscillators transmits an ultrasound wave in accordance with a drive signal supplied from the transmission/reception circuit 12 and receives an ultrasound echo from a subject to output a reception signal based on the ultrasound echo. Each ultrasound oscillator is configured, for example, by forming electrodes at both ends of a piezoelectric body made of a piezoelectric ceramic represented by lead zirconate titanate (PZT), a polymer piezoelectric element represented by poly vinylidene di fluid (PVDF), a piezoelectric single crystal represented by lead magnesium niobate-lead titanate (PMN-PT), or the like.

The ultrasound image data acquisition unit 19 transmits and receives the ultrasound wave using the first transducer array 11A to acquire first ultrasound image data. Further, the ultrasound image data acquisition unit 19 transmits and receives the ultrasound wave using the second transducer array 11B to acquire second ultrasound image data.

Here, the first ultrasound image data is data in which so-called beam forming processing is performed on the reception signal generated by the first transducer array 11A receiving the so-called ultrasound echo. Further, the second ultrasound image data is data in which the beam forming processing is performed on the reception signal generated by the second transducer array 11B receiving the ultrasound echo.

Under the control of the transmission/reception control unit 21, the transmission/reception circuit 12 transmits the ultrasound wave from the first transducer array 11A and performs processing on the signal acquired by the first transducer array 11A. Further, under the control of the transmission/reception control unit 21, the transmission/reception circuit 12 transmits the ultrasound wave from the second transducer array 11B and performs processing on the signal acquired by the second transducer array 11B.

Figure 4:
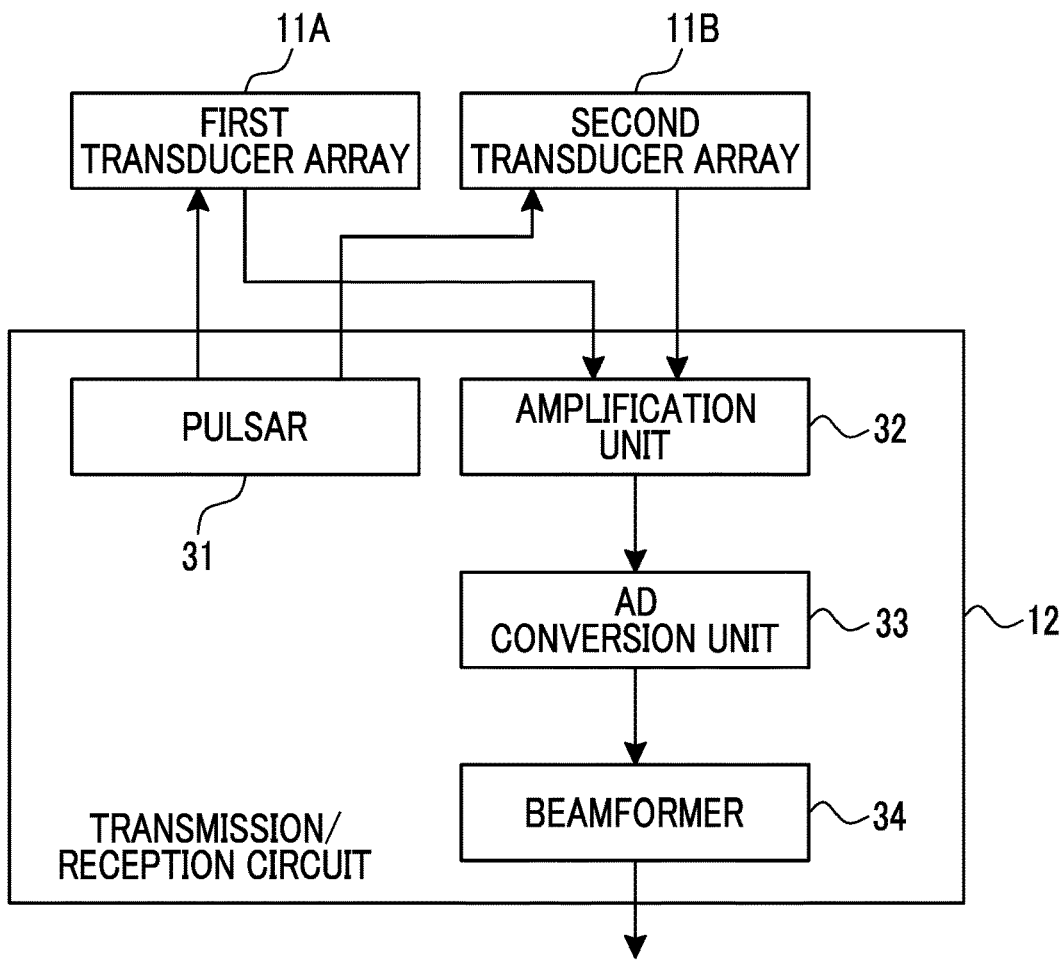
FIG. 4 is a schematic diagram showing an internal configuration of a transmission/reception circuit 12 shown in FIG. 1.

FIG. 4 is a schematic diagram showing an internal configuration of the transmission/reception circuit 12 shown in FIG. 1. The transmission/reception circuit 12 has a pulsar 31 connected to the first transducer array 11A and the second transducer array 11B. The transmission/reception circuit 12 includes an amplification unit 32 connected to the first transducer array 11A and the second transducer array 11B, an analog to digital (AD) conversion unit 33, and a beamformer 34.

The pulsar 31 includes, for example, a plurality of pulse generators and supplies respective drive signals to the plurality of ultrasound oscillators with a delay amount adjusted such that ultrasound waves transmitted from the plurality of ultrasound oscillators of the first transducer array 11A form an ultrasound beam, based on a transmission delay pattern selected in accordance with a control signal from the transmission/reception control unit 21. As described above, in a case where a pulse-like or continuous wave-like voltage is applied to the ultrasound oscillator electrodes of the first transducer array 11A, the piezoelectric body expands and contracts to generate pulse-like or continuous wave-like ultrasound waves from the respective ultrasound oscillators and the ultrasound beam is formed from a combined wave of the ultrasound waves.

The transmitted ultrasound beam is reflected by, for example, an examination target (internal organs or the like) in the subject, such as a human or an animal, and propagates toward the first transducer array 11A. The ultrasound echo propagating toward the first transducer array 11A in this manner is received by each of the ultrasound oscillators constituting the first transducer array 11A. In this case, each of the ultrasound oscillators constituting the first transducer array 11A expands and contracts by receiving the propagating ultrasound echo to generate the reception signal, which is an electric signal, and outputs the reception signal to the amplification unit 32.

The pulsar 31 also supplies the drive signal to the second transducer array 11B in the same manner as in the case of the first transducer array 11A with the delay amount adjusted, under the control of the transmission/reception control unit 21. Accordingly, the ultrasound beam is transmitted from the second transducer array 11B into the subject. Further, the second transducer array 11B receives the ultrasound echo propagating in the subject to generate the reception signal in the same manner as the first transducer array 11A. The reception signal generated by the second transducer array 11B is output to the amplification unit 32 in the same manner as the reception signal generated by the first transducer array 11A.

The amplification unit 32 amplifies the signal input from each of the ultrasound oscillators constituting the first transducer array 11A and transmits the amplified signal to the AD conversion unit 33. Further, the amplification unit 32 amplifies the signal input from each of the ultrasound oscillators constituting the second transducer array 11B and transmits the amplified signal to the AD conversion unit 33.

The AD conversion unit 33 converts the signal transmitted from the amplification unit 32 into a digital format. The beamformer 34 performs so-called reception focus processing of applying respective delays to respective reception signals in the digital format received from the AD conversion unit 33 and of adding the respective reception signals. The ultrasound image data which is a reception signal in which the respective reception signals converted by the AD conversion unit 33 are phase-adjusted and added and focus of the ultrasound echo is narrowed down is acquired by the reception focus processing.

The transmission/reception control unit 21 controls the transmission/reception circuit 12 to operate any one the first transducer array 11A and the second transducer array 11B according to used array information (information indicating whether the first transducer array 11A or the second transducer array 11B is used) among pieces of information input from the input apparatus 18.

In a case where the used array information (hereinafter, referred to as first used array information) indicating that the examination is performed using the first transducer array 11A is acquired from the input apparatus 18, the transmission/reception control unit 21 controls the transmission/reception circuit 12 to operate the first transducer array 11A. Further, in a case where the used array information (hereinafter, referred to as second used array information) indicating that the examination is performed using the second transducer array 11B is acquired from the input apparatus 18, the transmission/reception control unit 21 controls the transmission/reception circuit 12 to operate the second transducer array 11B.

The user selects a type of the transducer array desired to be used from a menu screen displayed on the display 15 to input the used array information to the processor 20, for example. In a case where the examination for the subject is performed, for example, there may be a case where a preset setting in which the type of the transducer array and an examination parameter according to a diagnostic purpose are set is used. In this case, a configuration may be employed in which in a case where the user selects the diagnostic purpose from the menu screen displayed on the display 15, the processor 20 applies the preset setting according to the diagnostic purpose and acquires the used array information included in the preset setting.

Figure 5:
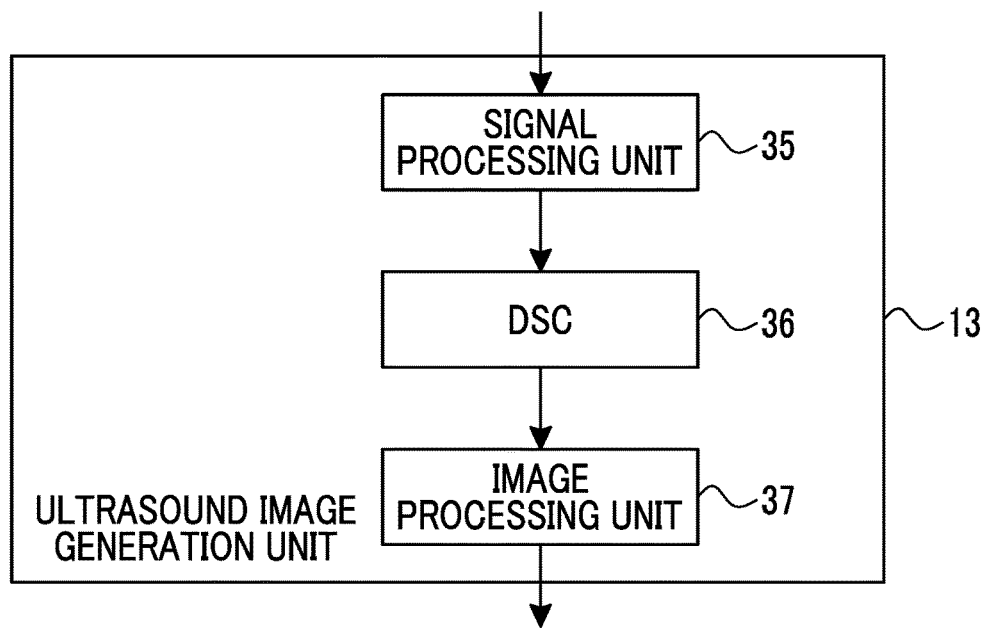
FIG. 5 is a schematic diagram showing details of an ultrasound image generation unit 13 shown in FIG. 1.

FIG. 5 is a schematic diagram showing details of the ultrasound image generation unit 13 shown in FIG. 1. The ultrasound image generation unit 13 includes a signal processing unit 35, a digital scan converter (DSC) 36, and an image processing unit 37. The signal processing unit 35 performs, on the ultrasound image data transmitted from the transmission/reception circuit 12, correction of attenuation by a distance according to a depth of a reflection position of the ultrasound wave and then envelope detection processing to generate a B-mode image signal, which is tomographic image information on a tissue in the subject.

The DSC 36 converts the B-mode image signal generated by the signal processing unit 35 into an image signal according to a normal television signal scanning method (raster conversion).

The image processing unit 37 performs various pieces of necessary image processing such as gradation processing on the B-mode image signal input from the DSC 36 and then transmits the B-mode image signal to the display control unit 14 in response to a command from the apparatus control unit 17. Hereinafter, the B-mode image signal subjected to the image processing by the image processing unit 37 will be simply referred to as an ultrasound image.

Under the control of the apparatus control unit 17, the display control unit 14 performs predetermined processing on the ultrasound image or the like generated by the ultrasound image generation unit 13 and displays the ultrasound image on the display 15.

Figure 6:
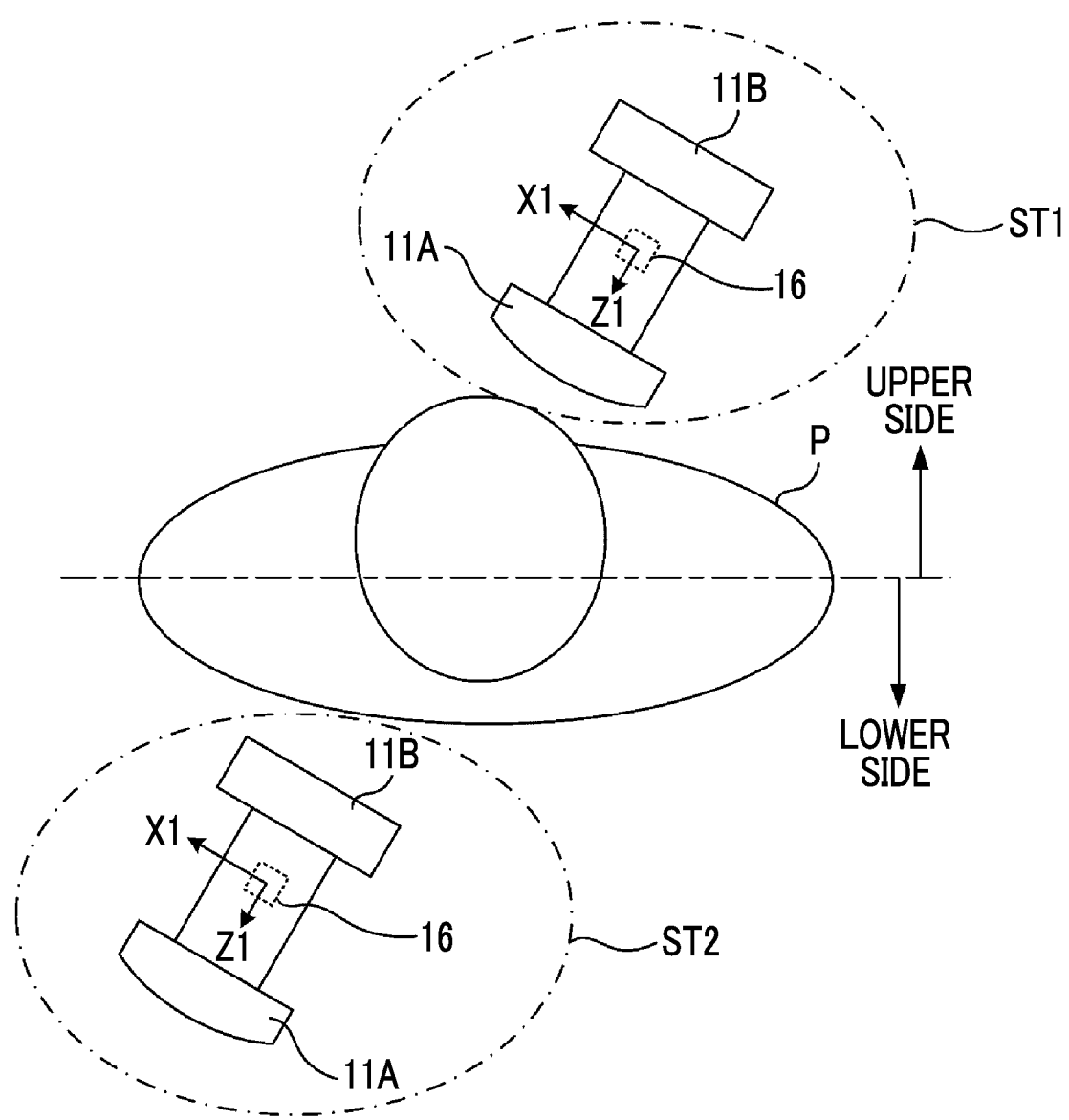
FIG. 6 is a schematic diagram showing an example of a use mode of the ultrasound probe 2.

FIG. 6 is a schematic diagram showing an example of a use mode of the ultrasound probe 2. FIG. 6 shows a subject P facing upward in the vertical direction. The position of the ultrasound probe 2 that can be taken with respect to the subject P is divided into, for example, a position on an upper side of the subject P and a position on a lower side of the subject P. FIG. 6 shows a use mode ST1 indicating an example of a case where the first transducer array 11A is brought into contact with the subject P from the upper side to perform the examination of the subject P and a use mode ST2 indicating an example of a case where the second transducer array 11B is brought into contact with the subject P from the lower side to perform the examination of the subject P. The angle of the ultrasound probe 2 with respect to the vertical direction in the use mode ST1 matches the angle of the ultrasound probe 2 with respect to the vertical direction in the use mode ST2. That is, the angle information of the ultrasound probe 2 derived based on the information output from the sensor 16 in the use mode ST1 matches the angle information of the ultrasound probe 2 derived based on the information output from the sensor 16 in the use mode ST2. Therefore, the use mode ST1 and the use mode ST2 are difficult to be identified only with the angle information derived from the output of the sensor 16.

In the present embodiment, the apparatus control unit 17 of the processor 20 acquires the angle information of the ultrasound probe 2 based on the output of the sensor 16 and determines the position of the ultrasound probe 2 with respect to the subject P based on the angle information and the used array information acquired in advance. Specifically, in a case where the angle information is acquired, the apparatus control unit 17 selects one of two position candidates (position on upper side of subject P and position on lower side of subject P), which are decided based on the angle information, based on the acquired used array information and determines the selected position candidate as the position of the ultrasound probe 2. In the example of FIG. 6, in a case where the acquired used array information is the first used array information, the apparatus control unit 17 determines that the use mode ST1 is used and determines that the position of the ultrasound probe 2 is the position on the upper side of the subject P. In a case where the acquired used array information is the second used array information, the apparatus control unit 17 determines that the use mode ST2 is used and determines that the position of the ultrasound probe 2 is the position on the lower side of the subject P.

Figure 7:
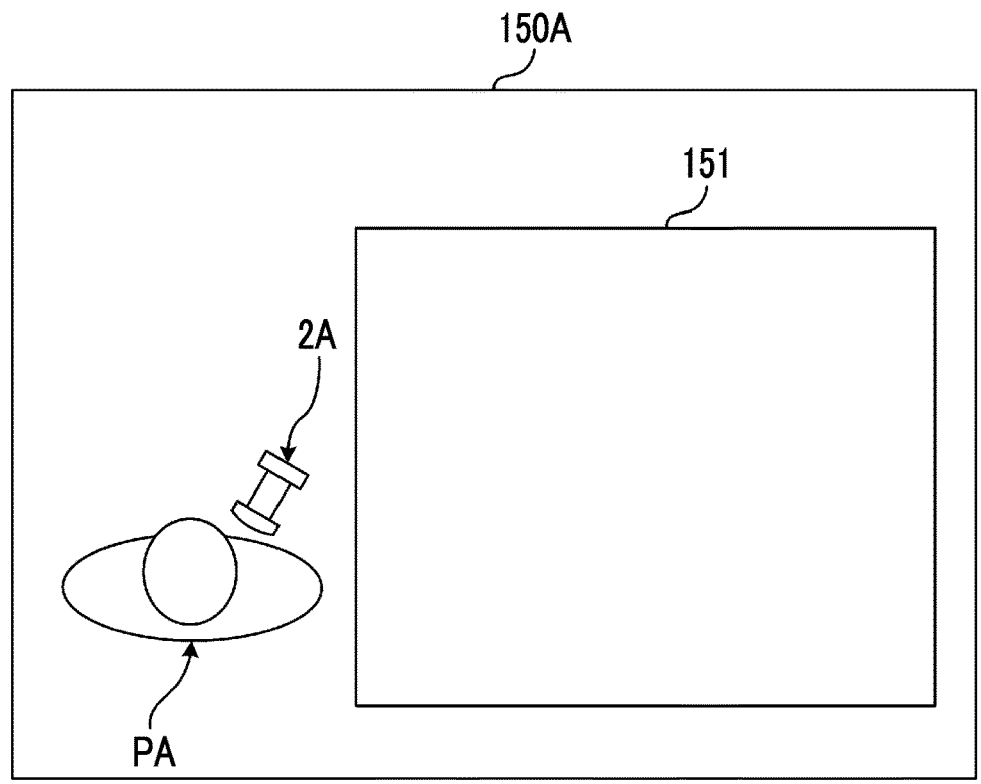
FIG. 7 is a diagram showing an example of a screen displayed on a display 15 under the control of an apparatus control unit 17.
Figure 7:
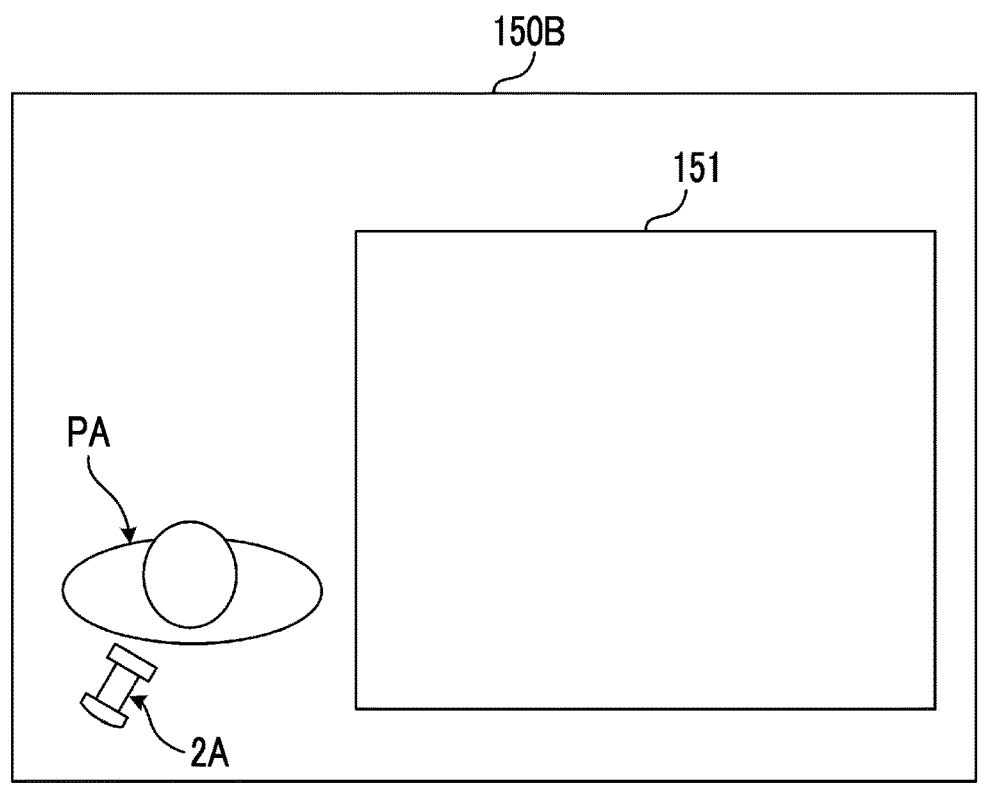

In a case where the position of the ultrasound probe 2 is determined, the apparatus control unit 17 performs control of causing the display 15 to display a subject image imitating the subject P and a probe image imitating the ultrasound probe 2 in a positional relationship corresponding to the determined position of the ultrasound probe 2, based on the determined position and the angle information acquired based on the output of the sensor 16. FIG. 7 is a diagram showing an example of a screen displayed on the display 15 under the control of the apparatus control unit 17. FIG. 7 shows a screen 150A in a case of the use mode ST1 and a screen 150B in a case of the use mode ST2.

Each of the screen 150A and the screen 150B includes an ultrasound image 151 and an auxiliary image including a subject image PA imitating the subject P and a probe image 2A imitating the ultrasound probe 2. A contact site of the subject P with which the ultrasound probe 2 is requested to be brought into contact is uniquely decided depending on the diagnostic purpose. That is, the position of the probe image 2A in the auxiliary image (position in width direction of subject image PA) is fixed, and only the angle (inclination) of the probe image 2A changes depending on a contact method of the housing H with the subject P.

In a case where the use mode ST1 is determined to be used (case where position of ultrasound probe 2 is determined to be upper side of subject P), the apparatus control unit 17 acquires a first template image corresponding to the use mode ST1. In the first template image, the probe image 2A in a state where the first transducer array 11A faces a subject image PA side is disposed at a predetermined position on the upper side of the subject image PA and in the width direction of the subject image PA. The apparatus control unit 17 generates auxiliary image data such that the angle of the probe image 2A in the first template image is an angle based on the acquired angle information, and displays the screen including the auxiliary image based on the auxiliary image data (screen 150A shown in FIG. 7) on the display 15.

In a case where the use mode ST2 is determined to be used (case where position of ultrasound probe 2 is determined to be lower side of subject P), the apparatus control unit 17 acquires a second template image corresponding to the use mode ST2. In the second template image, the probe image 2A in a state where the second transducer array 11B faces the subject image PA side is disposed at a predetermined position on the lower side of the subject image PA and in the width direction of the subject image PA. The apparatus control unit 17 generates auxiliary image data such that the angle of the probe image 2A in the second template image is an angle based on the acquired angle information, and displays the screen including the auxiliary image based on the auxiliary image data (screen 150B shown in FIG. 7) on the display 15.

As described above, with addition of the used array information in addition to the angle information based on the output of the sensor 16, the position of the ultrasound probe 2 with respect to the subject P can be accurately determined. A method of transmitting, to the processor 20 via the input apparatus 18, whether the use mode ST1 or the use mode ST2 is used is also assumed. However, according to the present embodiment, the use mode ST1 and the use mode ST2 can be automatically identified without the need for such an operation. Therefore, for example, in a case of performing an examination in which the position of the ultrasound probe 2 is changed above and below the subject P, the efficiency of the examination can be improved.

The apparatus control unit 17 may perform control of making notification of the moving direction of the ultrasound probe 2 (in other words, housing H) based on the ultrasound image data acquired after an examination start and the position of the ultrasound probe 2 determined as described above. For example, in a case where the acquired ultrasound image data is analyzed and determination is made that the ultrasound image data is not image data of an optimum cross section of a site to be examined, the apparatus control unit 17 derives the moving direction (rotation direction of housing H with transducer array on side in contact with subject P as a fulcrum) of the ultrasound probe 2 necessary for obtaining the image data of the optimum cross section thereof and displays an arrow image showing the rotation direction on the display 15.

Figure 8:
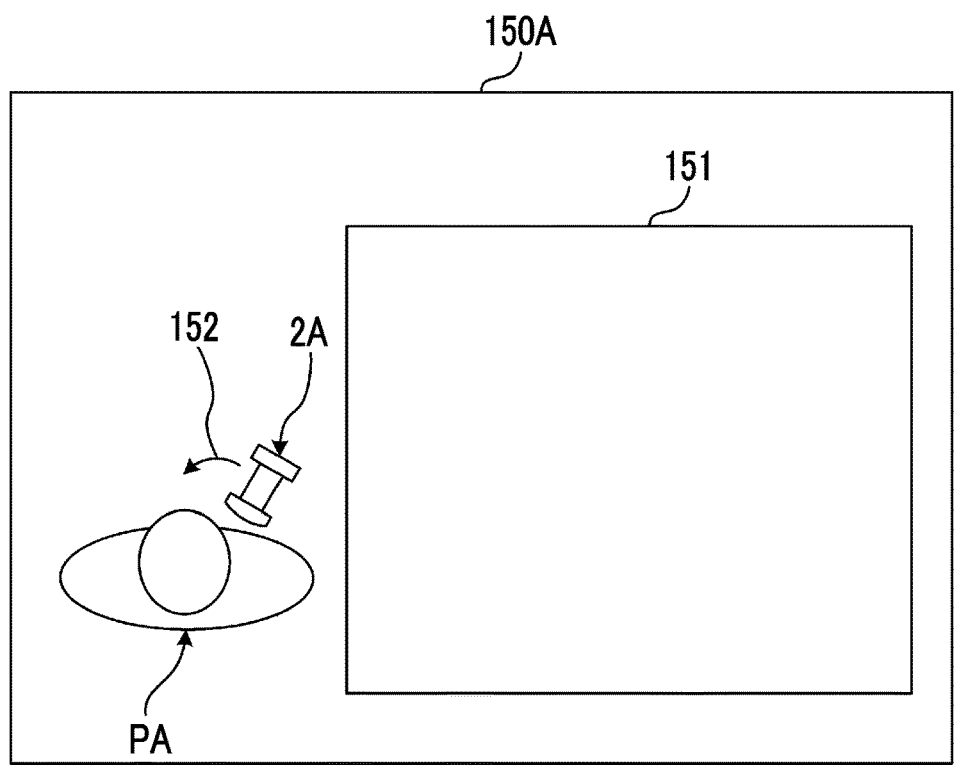
FIG. 8 is a diagram showing an example of the screen displayed on the display 15 under the control of the apparatus control unit 17.
Figure 8:
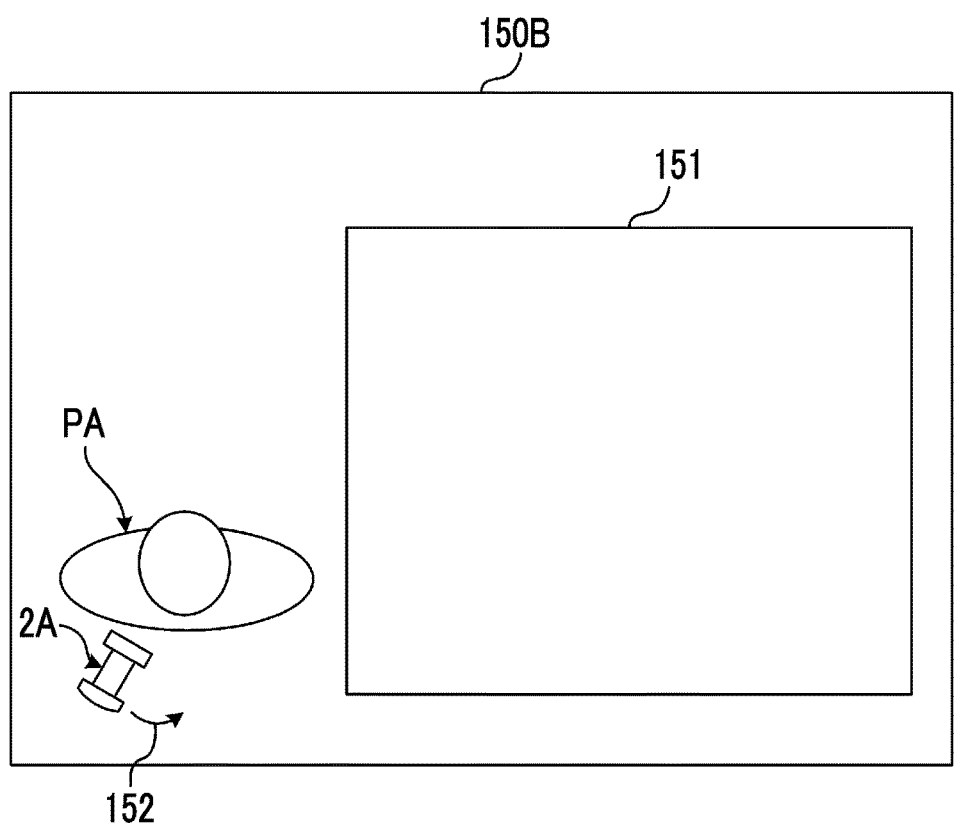

FIG. 8 is a diagram showing an example of the screen displayed on the display 15 under the control of the apparatus control unit 17. The screens 150A and 150B shown in FIG. 8 are the same as the screens 150A and 150B shown in FIG. 7 except that an arrow image 152 is added. In the example shown in FIG. 8, in a case of the use mode ST1, the arrow image 152 indicates that the probe is tilted toward a left half body side of the subject P. In a case of the use mode ST2, the arrow image 152 indicates that the probe is tilted toward a right half body side of the subject P. The moving direction of the ultrasound probe 2 necessary for obtaining the optimum cross section may also change depending on whether the use mode ST1 or the use mode ST2 is used.

Therefore, even in a case where assistance for obtaining such an optimum cross section is performed, the user can be instructed on an appropriate rotation direction by identifying the use mode ST1 and the use mode ST2.

In a case where the ultrasound probe 2 is rotated by the user according to the arrow image 152 shown in FIG. 8, the apparatus control unit 17 may analyze the ultrasound image data acquired after the rotation to determine whether or not the ultrasound image data is the image data of the optimum cross section. In a case where the ultrasound image data is not the image data of the optimum cross section, the arrow image may be continuously displayed on the display 15. In a case where the acquired ultrasound image data is determined to be the image data of the optimum cross section, the display of the arrow image may be stopped or an icon indicating that the image data of the optimum cross section has been obtained may be displayed on the display 15.

The apparatus control unit 17 may display the arrow image for issuing an instruction on the rotation direction of the ultrasound probe 2 necessary for measuring a volume of the site to be examined, instead of the display of the arrow image for obtaining the optimum cross section. Further, the apparatus control unit 17 may acquire the ultrasound image data at each rotation position in a case where the ultrasound probe 2 is rotated and angle information of the ultrasound probe 2 and generate three-dimensional image data based on a plurality of pieces of acquired ultrasound image data and the angle information corresponding to the ultrasound image data. Further, the apparatus control unit 17 may derive the volume of the site to be examined included in the three-dimensional image data from the generated three-dimensional image data and display the volume on the display 15 or save the volume in the memory. For example, even in a case where a generation algorithm of the three-dimensional image data and a derivation algorithm of the volume of the site to be examined differ between the use mode ST1 and the use mode ST2, the use mode ST1 and the use mode ST2 are identified and then the generation of the three-dimensional image data or the derivation of the volume is performed by an algorithm corresponding to the position of the ultrasound probe 2 to accurately perform the generation of the three-dimensional image data or the derivation of the volume.

Figure 9:
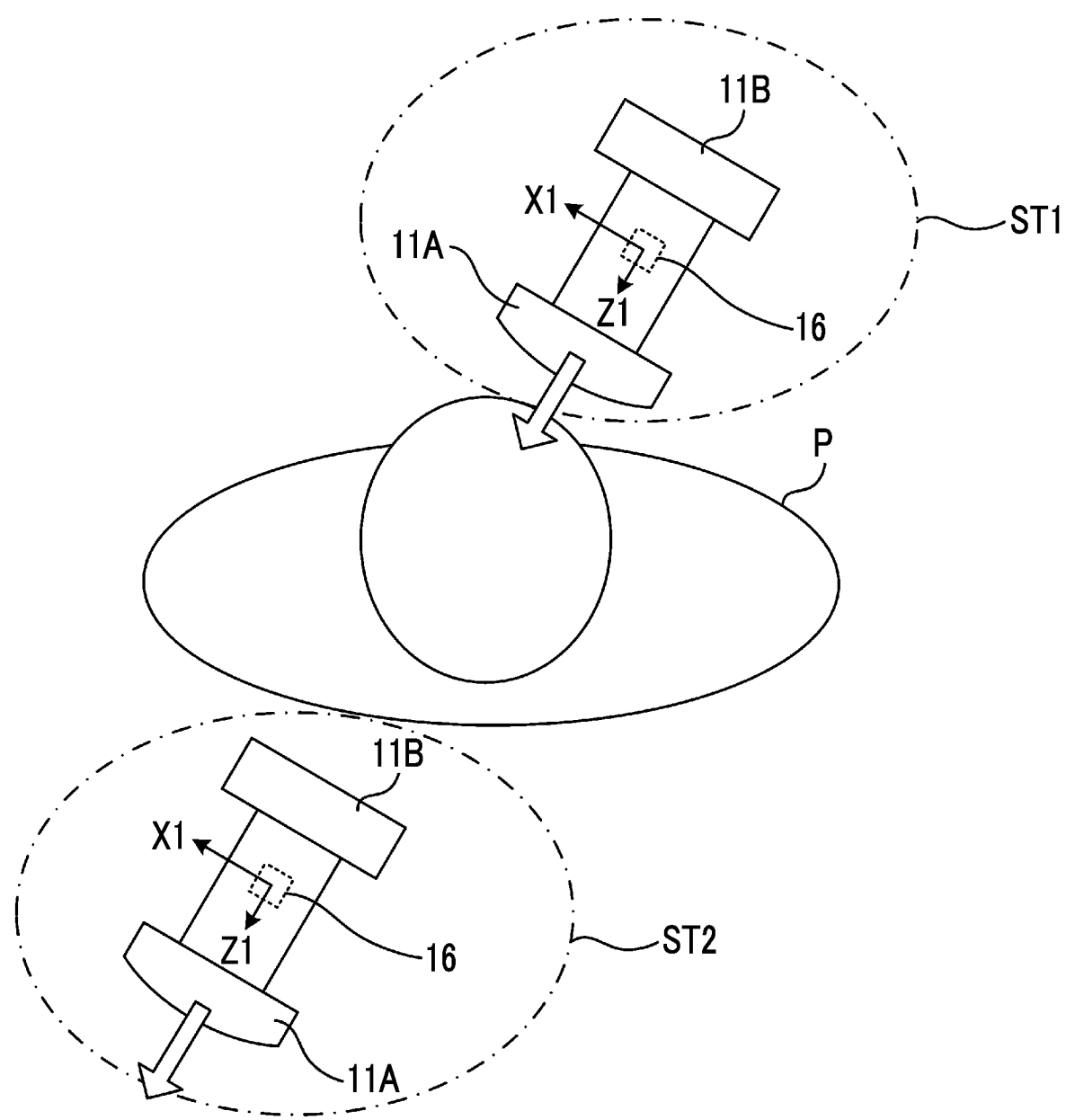
FIG. 9 is a schematic diagram showing an example in a case where the ultrasound probe 2 is moved in the same direction in each of a use mode ST1 and a use mode ST2 shown in FIG. 6.
Figure 10:
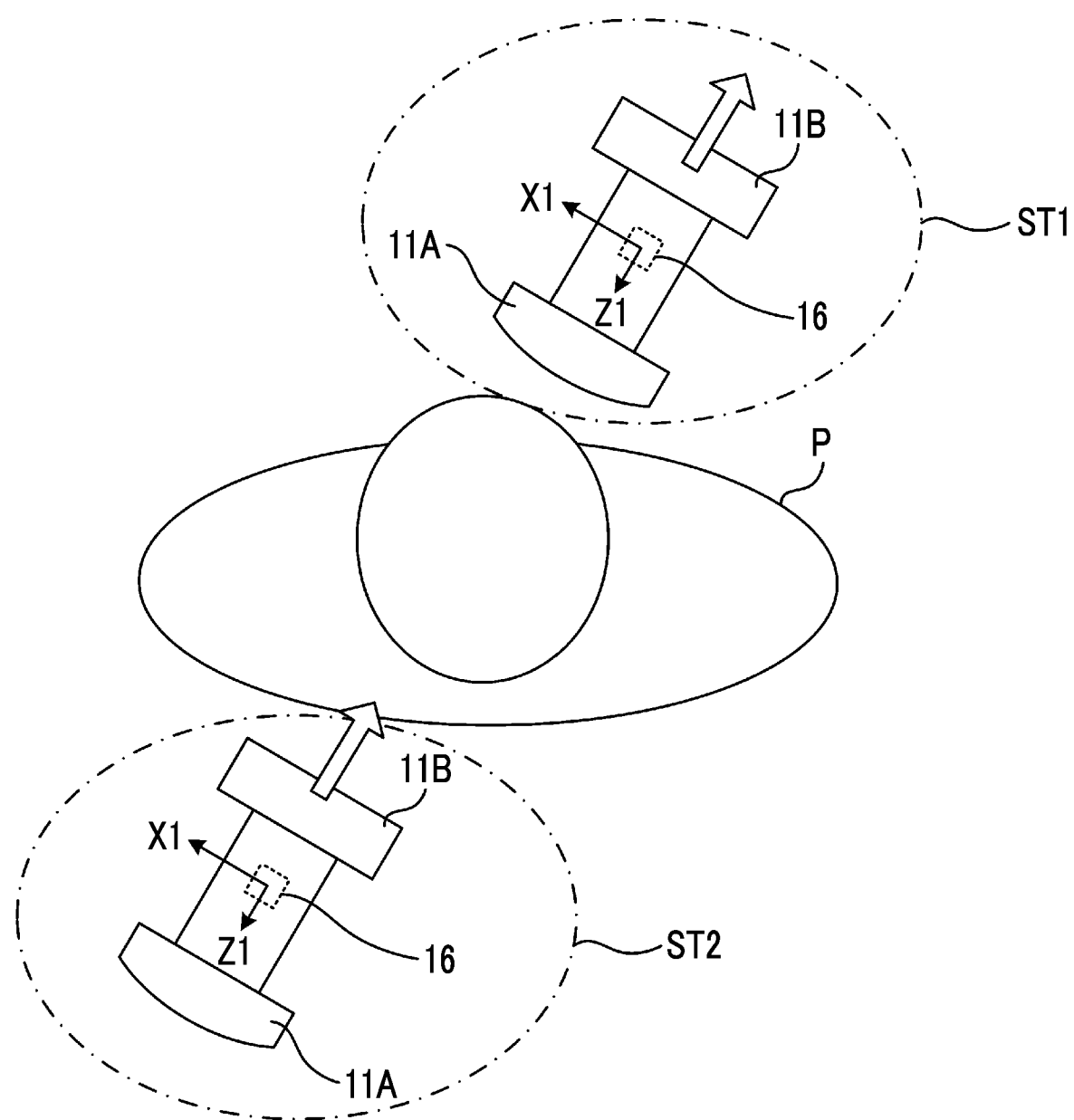
FIG. 10 is a schematic diagram showing an example in a case where the ultrasound probe 2 is moved in a direction opposite to that in FIG. 9 in each of the use mode ST1 and the use mode ST2 shown in FIG. 6.

The apparatus control unit 17 can also identify the motion of the ultrasound probe 2 with respect to the subject P based on the motion information of the ultrasound probe 2 based on the output of the sensor 16 and the used array information. FIG. 9 is a schematic diagram showing an example in a case where the ultrasound probe 2 is moved in the same direction in each of the use mode ST1 and the use mode ST2 shown in FIG. 6. FIG. 10 is a schematic diagram showing an example in a case where the ultrasound probe 2 is moved in a direction opposite to that in FIG. 9 in each of the use mode ST1 and the use mode ST2 shown in FIG. 6.

In the use mode ST1 shown in FIG. 9, the ultrasound probe 2 is moved in a direction approaching the subject P. Further, in the use mode ST2 shown in FIG. 9, the ultrasound probe 2 is moved in a direction away from the subject P. In both the use mode ST1 and the use mode ST2 shown in FIG. 9, information on an identical acceleration in the Z1 direction is output from the sensor 16. Therefore, the use mode ST1 and the use mode ST2 are difficult to be identified only by the motion information of the ultrasound probe 2 derived from the output of the sensor 16.

In the present embodiment, the apparatus control unit 17 acquires the motion information of the ultrasound probe 2 based on the output of the sensor 16 to determine the motion of the ultrasound probe 2 with respect to the subject P based on the motion information and the used array information acquired in advance. Specifically, in a case where the motion information is acquired, the apparatus control unit 17 selects one of two motion candidates (motion approaching subject P and motion away from subject P), which are decided based on the motion information, based on the acquired used array information and determines the selected motion candidate as the motion of the ultrasound probe 2. In the example of FIG. 9, the motion information of the ultrasound probe 2 acquired by the apparatus control unit 17 indicates the movement in the Z1 direction. In a case where the motion information indicates the movement in the Z1 direction and the acquired used array information is the first used array information, the apparatus control unit 17 determines that the ultrasound probe 2 moves in the direction approaching the subject P. In a case where the motion information indicates the movement in the Z1 direction and the acquired used array information is the second used array information, the apparatus control unit 17 determines that the ultrasound probe 2 moves in the direction away from the subject P.

In the example of FIG. 10, the motion information of the ultrasound probe 2 acquired by the apparatus control unit 17 indicates the movement in the Z2 direction. In a case where the motion information indicates the movement in the Z2 direction and the acquired used array information is the first used array information, the apparatus control unit 17 determines that the ultrasound probe 2 moves in the direction away from the subject P. In a case where the motion information indicates the movement in the Z2 direction and the acquired used array information is the second used array information, the apparatus control unit 17 determines that the ultrasound probe 2 moves in the direction approaching the subject P.

In a case where the ultrasound probe 2 is moved in the X direction or the Y direction, the apparatus control unit 17 determines that the ultrasound probe 2 has moved in the X direction or the Y direction based on the information of the acceleration in the X direction or the Y direction output from the sensor 16.

The apparatus control unit 17 executes processing associated with the motion of the ultrasound probe 2 identified as described above. In the ultrasound diagnostic apparatus 1, for example, first processing is associated with the motion of the ultrasound probe 2 away from the subject P in advance, second processing is associated with the motion of the ultrasound probe 2 approaching the subject P in advance, and third processing is associated with the motion of the ultrasound probe 2 in the X direction in advance. Contents of the first processing, the second processing, and the third processing are predetermined, but the following contents are preferable, for example.

First processing: processing of stopping update of the display of the ultrasound image data on the display 15 (processing of freezing ultrasound image data being displayed)

Second processing: processing of resuming the update of the ultrasound image data on the display 15 (processing of releasing the stop (freeze) of the display update by second processing)

Third processing: processing for saving the ultrasound image data in the memory

As described above, with addition of the used array information in addition to the motion information based on the output of the sensor 16, the motion of the ultrasound probe 2 with respect to the subject P can be accurately determined. A method of transmitting, to the processor 20 via the input apparatus 18, whether the use mode ST1 or the use mode ST2 is used is also assumed. However, according to the present embodiment, the motion of the ultrasound probe 2 can be automatically identified without the need for such an operation.

The apparatus control unit 17 may turn on power of the apparatus body 3 by using the motion information based on the output of the sensor 16. For example, in a case where a state where the acceleration in the Z1 direction or the Z2 direction detected by the sensor 16 is equal to or larger than a certain value is continued for a certain period of time, the apparatus control unit 17 turns on the power of the apparatus body 3. In a case where the angle of the ultrasound probe 2 derived based on the output of the sensor 16 or the acceleration in the Z1 direction or the Z2 direction detected by the sensor 16 continuously changes, the apparatus control unit 17 may turn on the power of the apparatus body 3. In a case where a state where the acceleration detected by the sensor 16 is equal to or less than a threshold value is continued for a certain period of time, the apparatus control unit 17 may turn off the power of the apparatus body 3.

The configuration of the ultrasound diagnostic apparatus 1 described above can be changed in various ways.

For example, the first transducer array 11A and the second transducer array 11B are of different types, but may be of an identical type but have different functions.

The apparatus control unit 17 acquires the used array information based on the information input from the input apparatus 18, but the present invention is not limited thereto. For example, with addition of a sensor apparatus that is disposed at one end T1 of the housing H and near the first transducer array 11A and recognizes contact between one end T1 of the housing H and a body surface of the subject and a sensor apparatus that is disposed at the other end T2 of the housing H and near the second transducer array 11B and recognizes contact between the other end T2 of the housing H and the body surface of the subject, determination may be made based on outputs of these sensor apparatuses whether the first transducer array 11A or the second transducer array 11B is used. Specifically, in a case where the sensor apparatus disposed at one end T1 of the housing H detects contact with an object, the apparatus control unit 17 determines that the first transducer array 11A is used and acquires the first used array information. On the other hand, in a case where the sensor apparatus disposed at the other end T2 of the housing H detects contact with an object, the apparatus control unit 17 may determine that the second transducer array 11B is used and acquire the second used array information.

Although FIGS. 1 and 2 show that the ultrasound probe 2 and the apparatus body 3 are connected by wire, the ultrasound probe 2 and the apparatus body 3 may be wirelessly connected.

Although the transmission/reception circuit 12 and the transmission/reception control unit 21 are included in the apparatus body 3, the transmission/reception circuit 12 and the transmission/reception control unit 21 may be included in the ultrasound probe 2 instead of being included in the apparatus body 3.

In the ultrasound image generation unit 13, the DSC 36 is connected to the signal processing unit 35 and the image processing unit 37 is connected to the DSC 36. However, the image processing unit 37 may be connected to the signal processing unit 35 and the DSC 36 may be connected to the image processing unit 37. In this case, the image processing unit 37 performs predetermined processing such as gradation processing on the B-mode image signal generated by the signal processing unit 35, and then the DSC 36 performs the raster conversion on the B-mode image signal. As described above, even in a case where the signal processing unit 35, the image processing unit 37, and the DSC 36 are connected in this order, the ultrasound image is generated in the ultrasound image generation unit 13 in the same manner as the case where the signal processing unit 35, the DSC 36, and the image processing unit 37 are connected in this order.

As described above, at least the following matters are described in the present specification. Although the components and the like corresponding to the above embodiments are shown in parentheses, the present invention is not limited thereto.

(1)

An ultrasound diagnostic apparatus (ultrasound diagnostic apparatus 1) comprising:

an ultrasound probe (ultrasound probe 2) including a housing (housing H) in which a first transducer array (first transducer array 11A) is disposed at one end (one end T1) and a second transducer array (second transducer array 11B) is disposed at the other end (the other end T2);

a sensor (sensor 16) that is provided in the housing and outputs information for acquiring motion information of the ultrasound probe or angle information of the ultrasound probe; and a processor (processor 20) that acquires used array information indicating which of the first transducer array and the second transducer array is used.

The processor is configured to acquire the motion information or the angle information based on the information outputted by the sensor and determine a motion or a position of the ultrasound probe with respect to a subject (subject P) based on the motion information or the angle information and the used array information.

According to (1), since the motion of the ultrasound probe with respect to the subject is determined based on the motion information acquired based on the output of the sensor and the used array information, the motion of the ultrasound probe can be accurately recognized. For example, even in a case where the output of the sensor is the same in a case where the ultrasound probe is located on one side with respect to the subject and the ultrasound probe moves in a direction approaching the subject in that state and in a case where the ultrasound probe is located on the other side with respect to the subject and the ultrasound probe moves in a direction away from the subject in that state, the motion of the ultrasound probe with respect to the subject can be determined based on the used array information. Further, according to (1), since the position of the ultrasound probe with respect to the subject is determined based on the angle information acquired based on the output of the sensor and the used array information, the position of the ultrasound probe can be accurately recognized. For example, even in a case where the output of the sensor is the same in a case where the ultrasound probe is located on one side with respect to the subject and in a case where the ultrasound probe is located on the other side with respect to the subject, the position of the ultrasound probe with respect to the subject can be determined based on the used array information.

(2)

The ultrasound diagnostic apparatus according to (1), in which the sensor is a sensor for acquiring the angle information, and the processor is configured to acquire the angle information based on the information outputted by the sensor and determine the position of the ultrasound probe with respect to the subject based on the angle information and the used array information.

(3)

The ultrasound diagnostic apparatus according to (2), in which the processor is configured to determine, as the position of the ultrasound probe, a position candidate based on the used array information among two position candidates of the ultrasound probe corresponding to the angle information.

(4)

The ultrasound diagnostic apparatus according to (2) or (3), in which the processor is configured to cause a display (display 15) to display a subject image (subject image PA) imitating the subject and a probe image (probe image 2A) imitating the ultrasound probe in a positional relationship corresponding to the determined position of the ultrasound probe.

(5)

The ultrasound diagnostic apparatus according to any one of (2) to (4), in which the processor is configured to:

acquire ultrasound image data by transmitting and receiving an ultrasound wave using any one of the first transducer array and the second transducer array; and perform control of making a notification of a moving direction of the ultrasound probe based on the determined position of the ultrasound probe and the ultrasound image data.

(6)

The ultrasound diagnostic apparatus according to any one of (2) to (4), in which the processor is configured to:

acquiring ultrasound image data by transmitting and receiving an ultrasound wave using any one of the first transducer array and the second transducer array; and generate three-dimensional image data based on the determined position of the ultrasound probe and the ultrasound image data.

(7)

The ultrasound diagnostic apparatus according to any one of (2) to (4), in which the processor is configured to:

acquire ultrasound image data by transmitting and receiving an ultrasound wave using any one of the first transducer array and the second transducer array; and derive a volume of a specific site included in the ultrasound image data based on the determined position of the ultrasound probe and the ultrasound image data.

(8)

The ultrasound diagnostic apparatus according to (1), in which the sensor is a sensor for acquiring the motion information, and the processor is configured to acquire the motion information based on the information outputted by the sensor and identify the motion of the ultrasound probe with respect to the subject based on the motion information and the used array information.

(9)

The ultrasound diagnostic apparatus according to (8), in which the processor is configured to execute processing associated with the identified motion.

(10)

The ultrasound diagnostic apparatus according to (9), in which the processor is configured to, with a used array of the first transducer array and the second transducer array as a first array and an unused array of the first transducer array and the second transducer array as a second array, identify a first motion in which the ultrasound probe moves in a direction from the first array toward the second array and a second motion in which the ultrasound probe moves in a direction from the second array toward the first array.

(11)

The ultrasound diagnostic apparatus according to (10), in which the processor is configured to execute first processing in a case where the motion of the ultrasound probe is determined to be the first motion and execute second processing different from the first processing in a case where the motion of the ultrasound probe is determined to be the second motion.

(12)

The ultrasound diagnostic apparatus according to (11), in which the processor is configured to acquire ultrasound image data by transmit and receive an ultrasound wave using any one of the first transducer array and the second transducer array and display the ultrasound image data on a display, the first processing is processing of stopping update of the display of the ultrasound image data on the display, and the second processing is processing of resuming the update.

(13)

The ultrasound diagnostic apparatus according to any one of (9) to (12), in which the processor is configured to:

based on the motion information, identify a third motion in which the ultrasound probe moves in a direction (X direction) intersecting a direction (Z direction) in which the first transducer array and the second transducer array are arranged; and execute third processing in a case where the motion of the ultrasound probe is determined to be the third motion.

(14)

The ultrasound diagnostic apparatus according to (13), in which the processor is configured to transmit and receive an ultrasound wave using any one of the first transducer array and the second transducer array to acquire ultrasound image data, and the third processing is processing of saving the ultrasound image data.

(15)

An operation method of an ultrasound diagnostic apparatus comprising:

in an ultrasound probe including a housing in which a first transducer array is disposed at one end and a second transducer array is disposed at the other end, acquiring used array information indicating which of the first transducer array and the second transducer array is used; and based on information outputted by a sensor that is provided in the housing and outputs information for acquiring motion information of the ultrasound probe or angle information of the ultrasound probe, acquiring the motion information or the angle information and determining a motion or a position of the ultrasound probe with respect to a subject based on the motion information or the angle information and the used array information.

EXPLANATION OF REFERENCES

1: ultrasound diagnostic apparatus
T1: one end
ST1, ST2: use mode
2A: probe image 2: ultrasound probe
T2: other end
3: apparatus body
11A: first transducer array
11B: second transducer array
12: transmission/reception circuit
13: ultrasound image generation unit
14: display control unit
15: display
16: sensor
17: apparatus control unit
18: input apparatus
19: ultrasound image data acquisition unit
20: processor
21: transmission/reception control unit
31: pulsar
32: amplification unit
33: AD conversion unit
34: beamformer
35: signal processing unit
36: DSC
37: image processing unit
150A, 150B: screen
151: ultrasound image
152: arrow image

What is claimed is:

1. An ultrasound diagnostic apparatus comprising:
an ultrasound probe including a housing in which a first transducer array is disposed at one end and a second transducer array is disposed at the other end;
a sensor that is provided in the housing and outputs information for acquiring motion information of the ultrasound probe or angle information of the ultrasound probe; and
a processor that acquires used array information indicating which of the first transducer array and the second transducer array is used,
wherein the processor is configured to acquire the motion information or the angle information based on the information outputted by the sensor and determine a motion or a position of the ultrasound probe with respect to a subject based on the used array information and one of the motion information or the angle information,
the first transducer array is a convex transducer array and the second transducer array is a linear transducer array,
the sensor is a sensor for acquiring the motion information,
the processor is configured to acquire the motion information based on the information outputted by the sensor and identify the motion of the ultrasound probe with respect to the subject based on the motion information and the used array information,
the processor is configured to execute processing associated with the identified motion,
the processor is configured to, with a used array of the first transducer array and the second transducer array as a first array and an unused array of the first transducer array and the second transducer array as a second array, identify a first motion in which the ultrasound probe moves in a direction from the first array toward the second array and a second motion in which the ultrasound probe moves in a direction from the second array toward the first array, and
the processor is configured to execute a first processing in a case where the motion of the ultrasound probe is determined to be the first motion and execute a second processing different from the first processing in a case where the motion of the ultrasound probe is determined to be the second motion.

2. The ultrasound diagnostic apparatus according to claim 1,
wherein the sensor is a sensor for acquiring the angle information, and
the processor is configured to acquire the angle information based on the information outputted by the sensor and determine the position of the ultrasound probe with respect to the subject based on the angle information and the used array information.

3. The ultrasound diagnostic apparatus according to claim 2,
wherein the processor is configured to determine, as the position of the ultrasound probe, a position candidate based on the used array information among two position candidates of the ultrasound probe corresponding to the angle information.

4. The ultrasound diagnostic apparatus according to claim 2,
wherein the processor is configured to cause a display to display a subject image imitating the subject and a probe image imitating the ultrasound probe in a positional relationship corresponding to the determined position of the ultrasound probe.

5. The ultrasound diagnostic apparatus according to claim 3,
wherein the processor is configured to cause a display to display a subject image imitating the subject and a probe image imitating the ultrasound probe in a positional relationship corresponding to the determined position of the ultrasound probe.

6. The ultrasound diagnostic apparatus according to claim 2,
wherein the processor is configured to:
acquire ultrasound image data by transmitting and receiving an ultrasound wave using any one of the first transducer array and the second transducer array; and
make a notification of a moving direction of the ultrasound probe based on the determined position of the ultrasound probe and the ultrasound image data.

7. The ultrasound diagnostic apparatus according to claim 2,
wherein the processor is configured to:
acquire ultrasound image data by transmitting and receiving an ultrasound wave using any one of the first transducer array and the second transducer array; and
generate three-dimensional image data based on the determined position of the ultrasound probe and the ultrasound image data.

8. The ultrasound diagnostic apparatus according to claim 2,
wherein the processor is configured to:
acquire ultrasound image data by transmitting and receiving an ultrasound wave using any one of the first transducer array and the second transducer array; and
derive a volume of a specific site included in the ultrasound image data based on the determined position of the ultrasound probe and the ultrasound image data.

9. The ultrasound diagnostic apparatus according to claim 1,
wherein the processor is configured to acquire ultrasound image data by transmitting and receiving an ultrasound wave using any one of the first transducer array and the second transducer array and display the ultrasound image data on a display, the first processing is a process of stopping an update of the display of the ultrasound image data on the display, and the second processing is a process of resuming the update.

10. The ultrasound diagnostic apparatus according to claim 1, wherein the processor is configured to:

based on the motion information, identify a third motion in which the ultrasound probe moves in a direction intersecting a direction in which the first transducer array and the second transducer array are arranged; and execute a third processing in a case where the motion of the ultrasound probe is determined to be the third motion.

11. The ultrasound diagnostic apparatus according to claim 10, wherein the processor is configured to acquire ultrasound image data by transmitting and receiving an ultrasound wave using any one of the first transducer array and the second transducer array, and the third processing is a process of saving the ultrasound image data.

12. An operation method of an ultrasound diagnostic apparatus comprising:

in an ultrasound probe including a housing in which a first transducer array is disposed at one end and a second transducer array is disposed at the other end, acquiring used array information indicating which of the first transducer array and the second transducer array is used; and based on information outputted by a sensor that is provided in the housing and outputs information for acquiring motion information of the ultrasound probe or angle information of the ultrasound probe, acquiring the motion information or the angle information and determining a motion or a position of the ultrasound probe with respect to a subject based on the used array information and one of the motion information or the angle information, wherein the first transducer array is a convex transducer array and the second transducer array is a linear transducer array, the sensor is a sensor for acquiring the motion information, and the operation method further comprises:

acquiring the motion information based on the information outputted by the sensor and identifying the motion of the ultrasound probe with respect to the subject based on the motion information and the used array information, executing processing associated with the identified motion, with a used array of the first transducer array and the second transducer array as a first array and an unused array of the first transducer array and the second transducer array as a second array, identifying a first motion in which the ultrasound probe moves in a direction from the first array toward the second array and a second motion in which the ultrasound probe moves in a direction from the second array toward the first array, and executing a first processing in a case where the motion of the ultrasound probe is determined to be the first motion and executing a second processing different from the first processing in a case where the motion of the ultrasound probe is determined to be the second motion.

* * * * *